United States Patent [19]

Kruse et al.

[11] Patent Number: 5,709,213
[45] Date of Patent: Jan. 20, 1998

[54] LOW NOISE, HIGH BANDWIDTH, AUGMENTED LEAD CIRCUIT FOR ACQUISITION OF CARDIAC PACING ARTIFACTS

[75] Inventors: John M. Kruse, New Brighton; Dave R. Jurek, Coon Rapids, both of Minn.

[73] Assignee: Medtronic, Inc., Minneapolis, Minn.

[21] Appl. No.: 714,910

[22] Filed: Sep. 17, 1996

[51] Int. Cl.$^6$ ................................................. A61B 5/0428
[52] U.S. Cl. ........................................... 128/696; 128/902
[58] Field of Search ..................................... 128/695, 696, 128/697, 901, 902; 607/27

[56] References Cited

U.S. PATENT DOCUMENTS

| | | | |
|---|---|---|---|
| 5,331,966 | 7/1994 | Bennet et al. | 128/696 |
| 5,377,687 | 1/1995 | Evans et al. | 128/700 |
| 5,379,775 | 1/1995 | Kruse | 128/697 |
| 5,435,316 | 7/1995 | Kruse | 128/697 |
| 5,448,997 | 9/1995 | Kruse et al. | 128/697 |

OTHER PUBLICATIONS

M. Simson, *The Role of Signal Averaged Electrocardiography in Identifying at High Risk for Lethal Ventricular Tacharrhythmias*, PACE, vol. 14, May 1991, Part II, pp. 944–950.

*Primary Examiner*—William E. Kamm
*Attorney, Agent, or Firm*—Thomas F. Woods; Harold R. Patton

[57] ABSTRACT

Disclosed are a method of and apparatus for deriving augmented lead electrocardiograph (ECG) signals from electrical signals sensed at three skin surface, limb electrodes attached to a patient's limbs without the use of a high impedance resistor network. First, second and third pairs of the three limb electrodes are combined to provide first, second and third positive and negative limb lead signal pairs. The first, second and third positive and negative limb lead signal pairs are combined and amplified to provide first, second, and third limb lead signals (LI, LII and LIII). The first, second and third amplified lead limb signals LI, LII and LIII are combined into augmented lead signals aVR, aVL, aVF through a low impedance resistor network and operational amplifiers, in accordance with the formulas: aVR=–0.5 (LI+LII), aVL=0.5 (LI–LIII), and aVF=0.5 (LII+LIII).

7 Claims, 7 Drawing Sheets

FIG. 1A
INPUT SURFACE ECG

FIG. 1B
ENLARGED PACING ARTIFACT

LOW NOISE, HIGH BANDWIDTH, AUGMENTED LEAD CIRCUIT FOR ACQUISITION OF CARDIAC PACING ARTIFACTS

FIELD OF THE INVENTION

This invention relates generally to the field of medical monitoring devices, and more particularly relates to medical devices used to process limb lead electrocardiograph (ECG or ECG) signals to derive augmented lead signals for use in conjunction with circuitry for detecting and discriminating low amplitude artifacts produced by artificial cardiac pacing from the patient's ECG and noise.

BACKGROUND OF THE INVENTION

Over the years, many implantable medical devices have been developed for monitoring a medical condition and/or providing a therapy to a patient. Such devices include electrical stimulation devices for stimulating body organs and tissue to evoke a response for enhancing a body function or to control pain and drug delivery devices for releasing a drug bolus at a selected site. Other more passive medical devices have been developed for simply monitoring a patient's condition. Cardiac pacemakers and other cardiac arrhythmia control devices are among the most widely known and clinically used implantable medical devices for delivering a therapy to a patient while monitoring a cardiac condition.

Early in the development of cardiac pacemakers, patient follow-up to monitor pacemaker operation was facilitated by telephonic transmissions of skin surface ECGs in real time to a physician's office employing such systems as the MEDTRONIC® TeleTrace® ECG transmitter. Over time, various patient worn, ambulatory ECG and device monitors have been developed for providing ECG data for analysis of cardiac arrhythmias. The skin surface signals picked up and processed in this monitoring operation include both the patient's cardiac activity or ECG and the pacing pulse "spike" or artifact as well as ambient noise, skin-electrode movement noise and internal circuit baseline noise.

Later, implantable pacemakers were designed to be programmable in operating mode and parameters employing "telemetry" transceivers in the implanted medical device and an external programmer. In current technology cardiac arrhythmia control devices, e.g. multi-programmable, cardiac pacemakers and pacemaker-cardioverter-defibrillators, a relatively wide range of device operating modes and parameters are remotely programmable to condition the device to diagnose one or more cardiac arrhythmias and deliver an appropriate therapy. In cardiac pacemakers, the pacing rate in one or both heart chambers is governed by algorithms that process the underlying cardiac rhythm as well as physiologic conditions, such as patient activity level and other measured variables, to arrive at a suitable pacing rate. The pacemaker operating modes and the algorithm for establishing the appropriate pacing rate are programmed into internal memory by accessing the implanted pacemaker's telemetry transceiver with an external programmer during a downlink telemetry transmission. Similarly, with pacemaker-cardioverter-defibrillator devices, the diagnosis of a tachyarrhythmia requiring delivery of a treatment therapy and the therapies to be delivered are governed by operating modes and algorithm parameters that may be programmed into device memory using such a programmer.

Moreover, such implanted devices have the capability to process the patient's electrogram and any measured physiological conditions employed in the diagnosis and to store the data, particularly such data that is related to a detected arrhythmic episode satisfying the criteria for treatment, for subsequent telemetry out or uplink telemetry on interrogation of the device memory by the external programmer. The telemetered out data is analyzed and may be employed to establish or refine the operating modes and parameters of the device operating algorithms by re-programming in the corresponding operating mode or parameter data.

Recent generation pacemaker programmers have incorporated both the uplink and downlink telemetry features for interrogating the implanted device memory and for programming the operating modes and parameters as described above with the ability to record the patient's ECG using at least three surface electrodes. The pacing artifact is also picked up in the composite signals taken from various combinations of skin surface electrodes. Such programmers include the MEDTRONIC® Model 9760 pacemaker programmer and the Model 9790 universal programmer for use in programming both bradycardia pacemakers and tachyarrhythmia devices.

The Model 9790 programmer, for example, employs a sub-set of skin electrodes used in the standard twelve lead ECG machine, namely the limb electrodes on the right arm (RA electrode), left arm (LA electrode), the left leg (LL electrode) and the right leg (RL) electrode. The ECG signals detected across selected combinations of the RA, LA and LL electrodes are characterized as "Leads". In a standard ECG procedure, a set of three "Bipolar Leads", denoted I, II and III, and a set of "Augmented Leads", denoted aVR, aVL and aVF, are derived from the voltages across these three limb electrodes or combinations of three limb electrodes as follows:

TABLE I

| I   | = LA – RA            | (1) |
|-----|----------------------|-----|
| II  | = LL – RA            | (2) |
| III | = LL – LA            | (3) |
| aVR | = RA – 0.5 (LA + LL) | (4) |
| aVL | = LA – 0.5 (LL + RA) | (5) |
| aVF | = LL – 0.5 (LA + RA) | (6) |

The definition of these leads or lead signals and others as well as certain requirements and performance standards are published by the Association for the Advancement of Medical Instrumentation (AAMI). In addition, an exhaustive description of the standardized twelve lead ECG technique is set forth in commonly assigned U.S. Pat. No. 5,377,687.

The Model 9790 programmer is also designed to allow the selective capture of the signal, designated lead $V_x$, from a precordial electrode that may be positioned by the physician at any one of the six precordial electrode positions described in detail in the above-referenced '687 patent. A common electrode is formed for the lead $V_x$ measurement by resistively coupling the LA, RA and LL electrodes together.

The Model 9790 programmer is additionally designed to support the analysis of small, high frequency waveforms, commonly called "late potentials" in the QRS complex, by signal averaged electrocardiography (SAECG) techniques as described by M. Simson in "The Role of Signal Averaged Electrocardiography in Identifying Patients at High Risk for Lethal Ventricular Tachyarrhythmias", *PACE*, vol. 14, pp. 944–950, May 1991, Part II. In this technique, skin surface electrodes are arranged in pairs in X, Y and Z axes to derive orthogonal sets of ECG signals that are averaged and processed as described in the Simson article. In the Model 9790 implementation, the LA electrode is denoted X+, the RA electrode is denoted X−, the LL electrode is denoted Y+ and three other skin electrodes are placed on the patient's body to provide the Y− electrode and the Z+ and Z− electrodes.

Electrical connections of the limb and precordial electrodes are depicted in commonly assigned U.S. Pat. No. 5,435,316 as inputs to a lead weighting resistor network and DEFIB/ESD protection block (in FIG. 1A of the '316 patent). As described in commonly assigned U.S. Pat. Nos. 5,379,775 and 5,448,997 and in the '316 patent, the ability to detect and discriminate the pacing artifact from noise and to reconstruct and display the ECG and a pacing pulse marker in separate displays is hampered by the difficulty of discriminating the high frequency pacing pulse signal components from noise. The high frequency signal components are caused by the narrow pulse widths of low energy pacing pulses.

In this regard, as pacing lead technology has evolved, chronic pacing thresholds for consistently achieving capture of the heart have approached very low energy values thereby dramatically allowing the reduction of delivered pace pulse amplitudes and pulse widths and of battery capacity and size while maintaining adequate longevity. The pacing pulse energy level is programmable through programming pacing width and, typically, voltage pulse peak amplitude. As pulse widths are narrowed to about 0.05 mS to 1.0 mS, the pace pulse signal exhibits much higher frequency components than the ECG and are difficult to distinguish from certain noise sources. These noise sources include, but are not limited to, noise generated from a pacemaker programming head having a carrier frequency of 175 kHz for example, noise generated from a switched mode power supply having a frequency range from 10 kHz to 10 MHz for example, as well as ambient noise from other equipment, muscle artifacts, etc. High speed OP Amps contained within the "leads I, II, III and X, Y, and Z amps." block 104 are configured to accurately detect such pacing artifacts, even in the presence of such multiple noise sources.

Figure 1A:
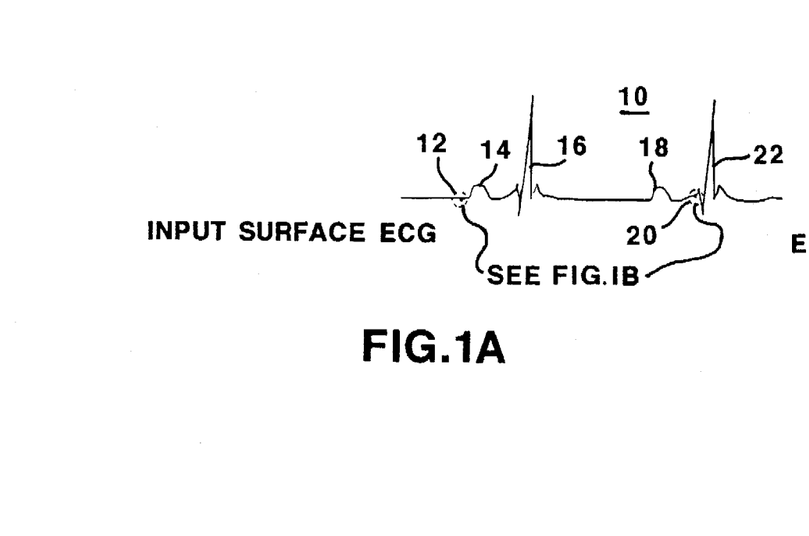
FIGS. 1A and 1B are graphical representations of a skin surface ECG tracing containing atrial and ventricular pacing pulses and cardiac depolarization waveforms.
Figure 1B:
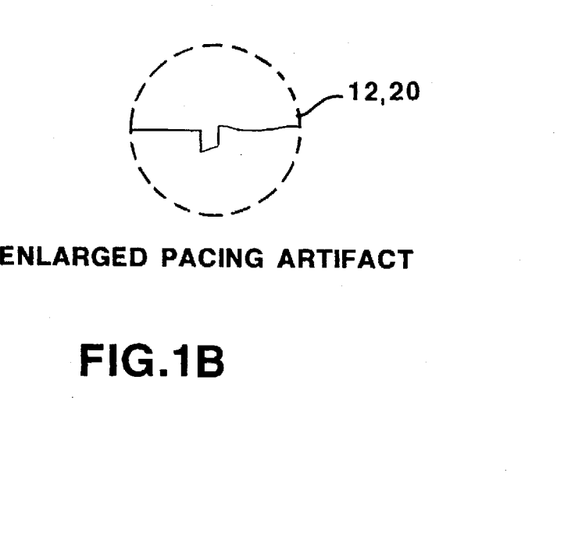

A graphical representation of an observed ECG signal 10 containing pacing artifacts is illustrated in FIGS. 1A and 1B. The electrical noise, including muscle artifacts and the other noise sources described above, have been removed in this illustration to better depict the amplitude, frequency and pulse width relationships of the signals of interest. In the first tracing of FIG. 1A, an elicited P-wave 14 immediately follows an atrial pacing pulse evidenced by an atrial pacing pulse artifact 12 in the ECG signal picked up with skin surface electrodes. A ventricular depolarization follows after the AV delay interval manifested as a conducted "QRS" complex or R-wave 16. In the third tracing, a ventricular pacing pulse artifact 20, indicating the delivery of a ventricular pacing pulse by the pacemaker pulse generator, appears at the end of the AV delay interval from the preceding P-wave 18. Capture of the heart by the ventricular pacing pulse is evidenced by the R-wave 22. It is important to note that the pacing pulse artifacts exhibited by the pacing pulses, when detected across pairs of skin surface electrodes, can exhibit a lower amplitude and much higher frequency components than either P-waves 14, 18 or R-waves 16, 22. This relationship alone tends to make pacing artifacts difficult to detect and distinguish from the elicited heart depolarization signals using prior art ECG monitoring devices, particularly where multiple noise sources are operating in a frequency spectrum identical to or nearly identical to the pacing artifact frequency spectrum.

As described in greater detail below, the calculation of the augmented lead values aVR, aVL and aVF in the prior art Model 9790 programmer involved the use of high impedance OP Amps in carrying out the algebraic processes. A high impedance (greater than a 3 megohm differential) must be maintained at the input to the circuit without dissipating a great deal of supply current. The noise floor of the circuitry must also be kept below 5 microvolts over a wide bandwidth. These requirements are difficult to meet concurrently.

Precision high impedance resistors in an impedance ladder tree (as described below in reference to FIG. 3B) have been employed in the signal lines at the + and − input terminals of the OP Amps to produce the appropriate voltage drops to execute the equations set forth above in TABLE I. The precision high impedance resistors are themselves "noisy" and add expense to the circuitry. The signal-to-noise ratio of the signals processed through the high impedance resistors can become too low to adequately identify the high frequency pacing artifact, particularly when the pacing artifact's frequency spectrum lies near the middle of the spectrum of noise generated by multiple noise generators.

SUMMARY OF THE INVENTION

The present invention overcomes the disadvantages of the prior art systems by providing a method of and apparatus for determining the augmented lead signal values aVR, aVL and aVF without using precision high impedance resistors thereby eliminating noise sources particularly affecting the detection of the pacing artifact from the augmented lead signals.

The present invention is realized in a method of and apparatus for deriving augmented lead electrocardiograph (ECG) signals from electrical signals sensed at three skin surface, limb electrodes attached to a patient's limbs without the use of a high impedance resistor network comprising the steps of and means for: combining first, second and third pairs of the three limb electrodes to provide first, second and third, positive and negative, limb lead signal pairs; combining and amplifying the first positive and negative limb lead signal pair into a first limb lead signal (LI); combining and amplifying the second positive and negative limb lead signal pair into a second limb lead signal (LII); combining and amplifying the third positive and negative limb lead signal pair into a third limb lead signal (LIII); and combining the first, second and third lead limb signals LI, LII and LIII into augmented lead signals through a low impedance resistor network and operational amplifier.

In particular, the method and apparatus of the invention are carded out by the steps of and means: sensing a first limb lead signal pair from the RA and LA limb electrodes; sensing a second limb lead signal pair from the RA and the LL limb electrode; sensing a third limb lead signal pair from the LA and LL limb electrodes; amplifying and subtracting the first limb lead signal pair to derive a first, amplified limb lead signal (LI); amplifying and subtracting the second limb lead signal pair to derive a second, amplified limb lead signal (LII); amplifying and subtracting the third limb lead signal pair to derive a third, amplified limb lead signal (LIII); deriving a first augmented lead signal (aVR) by combining the first and second limb lead signals in a first low impedance network and amplifier in accordance with the formula aVR=−0.5(LI+LII); deriving a second augmented lead signal (aVL) by combining the first and third limb lead signals in a second low impedance network and amplifier in accordance with the formula aVL=0.5(LI−LIII); and deriving a third augmented lead signal (aVF) by combining the second and third limb lead signals in a third low impedance network and amplifier in accordance with the formula aVF=0.5(LII+LIII).

Pacing artifact detection from the augmented lead signals is enhanced by the elimination of the high impedance resistor network noise source. The pacing artifact signal detection can be accomplished at amplitudes several times smaller than previously known techniques. The present invention operates in conjunction with the inventions patented in the above-referenced '687, '997 and '316 patents.

BRIEF DESCRIPTION OF THE DRAWINGS

Other objects and advantages of the present invention will be readily appreciated by reference to the following detailed description and the accompanying drawings, in which like reference numerals designate like parts throughout the figures thereof and wherein.

DETAILED DESCRIPTION OF THE PREFERRED EMBODIMENT

In accordance with the present invention, circuitry for calculating the aVR, aVL and aVF lead signal values is simplified and made more economical while ensuring a high signal-to-noise level facilitating detection and discrimination of the pace pulse artifact from the composite ECG and noise signals at the RA, LA and LL electrodes. The present invention is incorporated into the system of FIGS. 1A and 1B in conjunction with the circuit blocks disclosed in the above-referenced '687, '997 and '316 patents, incorporated herein by reference. The following description of the preferred embodiment is presented in that context, first describing relevant portions of the current Model 9790 circuit and then describing the improved circuit portion incorporating the invention.

Figure 2A:
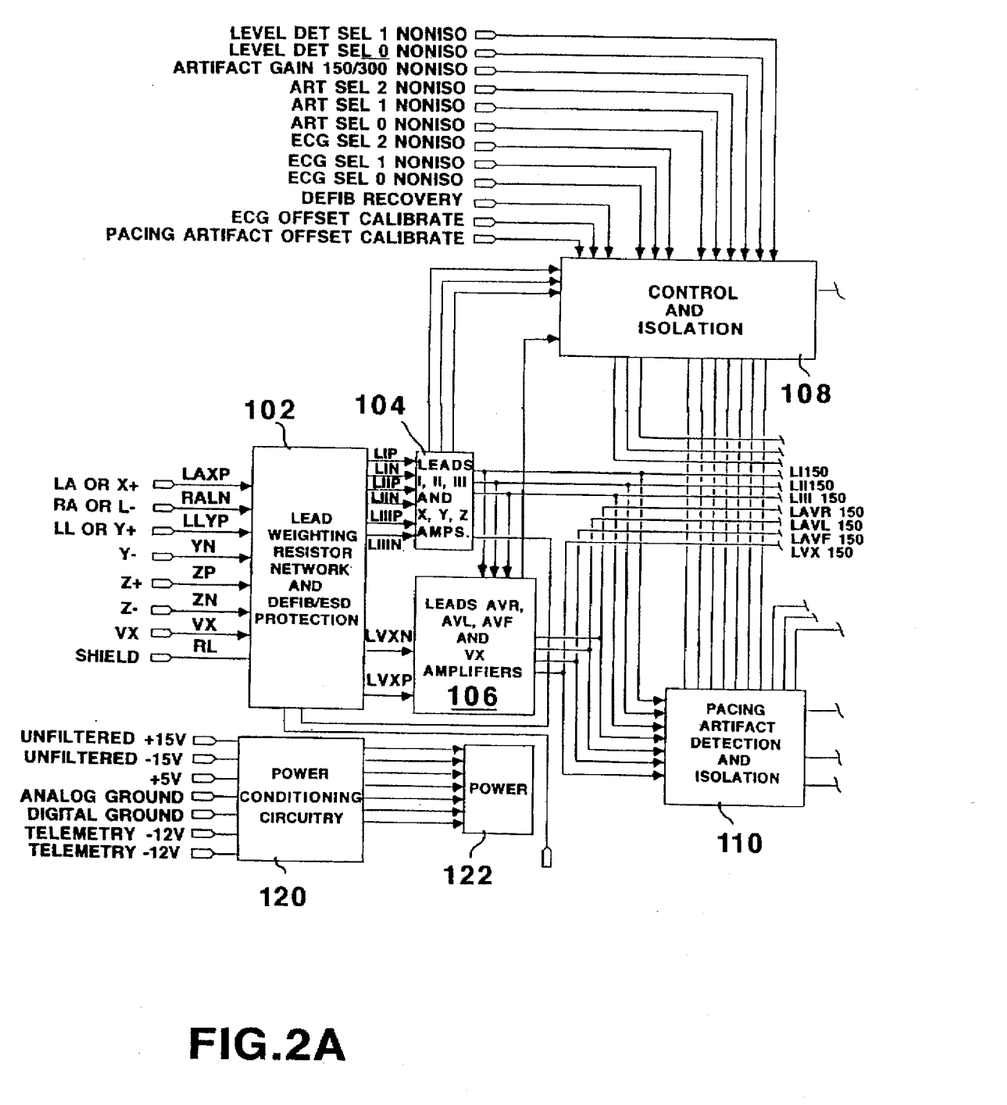
FIGS. 2A and 2B together constitute a block diagram illustrating one embodiment of a system in which the present invention may be embodied for processing the augmented leads and for detecting low amplitude pacemaker pacing artifacts within the augmented leads.
Figure 2B:
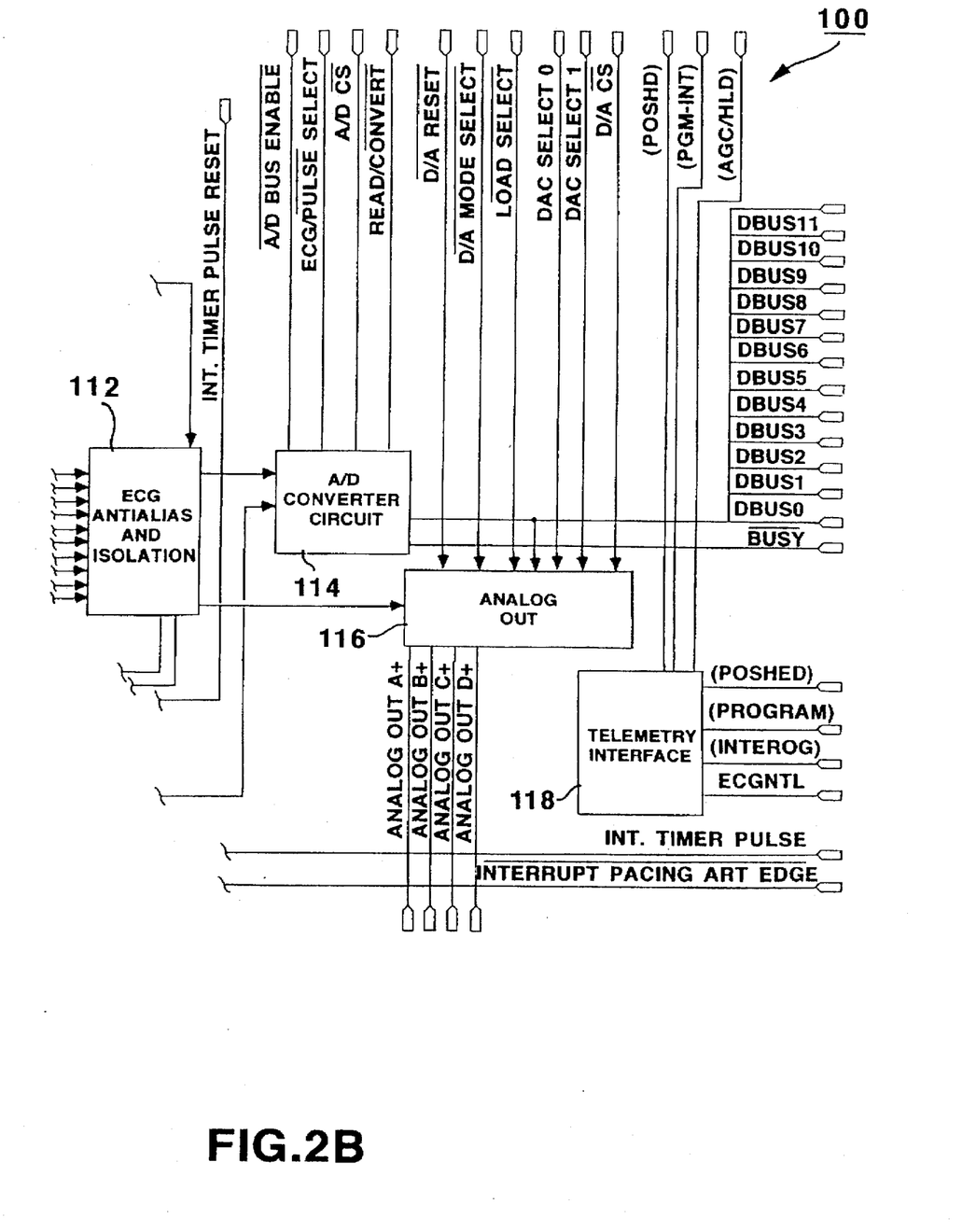

FIGS. 2A and 2B taken together are a block diagram illustrating the system 100 also depicted in the above-referenced '316 patent, incorporated herein by reference in its entirety in which the present invention is realized for detecting low amplitude pacemaker pacing artifacts, wherein the pacing artifacts have a frequency spectrum which lies in the middle of a spectrum of noise produced by a plurality of noise sources. The system 100 includes several circuit blocks forming the ECG and pacing artifact processing circuitry of the Model 9790 programmer of which only certain blocks are changed in accordance with the present invention and are described in detail. The blocks of the system 100 are powered by "power conditioning circuitry" block 120 and "power" block 122 and also include a "telemetry interface" block 118 which operates independently of the remaining circuit blocks and is not relevant to the present invention.

Referring to the overall operation of the programmer system 100 in FIG. 2A, the RA, LA, RL and LL electrodes and the Y–, Z+, Z– and $V_x$ electrodes, if present, are coupled through cables to the input terminals of "lead weighting resistor network and DEFIB/ESD protection" block 102. The patient is "grounded" when lying on the table, but is not grounded to the system 100 to avoid leakage current problems. Instead, the right leg or RL electrode is coupled to a driven right leg high speed op amp in block 102 that injects inverted common mode noise signals into the patient's body to counter common node noise up to and above 10 Mhz as described in the above-incorporated '316 patent.

For convenience, the signals on the other limb electrodes are referred to as follows in parentheses: LA or X+ (LAXP); RA or L– (RAXN); LL or Y+ (LLYP); Y– (YN); Z+ (ZP); Z– (ZN); and $V_x$ (VX). The signals LAXP, RAXN, LAXP, YN, ZP, and ZN are combined in circuitry in block 102 as described below to develop positive and negative pairs of bipolar lead I, II and III signals that are applied to the "leads I, II, III and X, Y, Z amps" block 104. In addition, a positive and negative pair of VX signals are developed in block 102 and applied to a Vx amplifier circuit within the "leads aVR, aVL, aVF and Vx amplifiers" block 106. At this point, it is noted that the prior art circuitry within block 102 as implemented in the Model 9790 programmer is shown and described below with respect to FIGS. 3A and 3B and the improvements thereto in accordance with the present invention are described below with respect to FIGS. 3A and 5.

In FIG. 2A, block 104 amplifies the bipolar lead I, II and III signals and applies them as the signals LI150, LII150, and LIII150 to block 106 as well as to the "ECG anti-alias and isolation" block 112 and the "pacing artifact detection and isolation" block 110. Block 104 also provides related signals to the control and isolation block 108 for defibrillation circuit protection. The circuitry within block 104 is described in detail in the above-incorporated '316 patent (FIG. 2) and is employed in the improved system of the present invention in conjunction with the improved circuitry of blocks 102 and 106 described hereafter.

It should be noted that the input signals to the three amplifier stages of block 104 of FIG. 2 of the '316 patents are incorrectly denoted in part. The correct notation is LIP (RA ELECTRODE) and LIN (LA ELECTRODE) for the first amplifier stage (as correctly shown), LIIP (LL ELECTRODE) and LIIP (RA ELECTRODE) for the second amplifier stage, and LIIIP (LL ELECTRODE) and LIIIN (LA ELECTRODE) for the third stage. These input signals are shown in FIGS. 3B and in FIG. 5 as described below.

Block 106 as implemented in the Model 9790 programmer is described below with respect to FIG. 4, and the improvements thereto in accordance with the present invention are described below in reference to FIG. 6. In accordance with the present invention, block 106 of FIG. 6 amplifies the augmented lead signals and applies them to the "ECG anti-alias and isolation" block 112 and the "pacing artifact detection and isolation" block 110 as signals LAVR150, LAVL150, LAVF150 and LVX150.

The detailed circuitry of block 110 for detecting the pacing artifact is set forth in the above-referenced '997 patent (FIGS. 3A and 3B) and in the above-referenced '775 patent (FIG. 2) and is not changed herein. The pacing pulse artifact detection and discrimination is accomplished in block 110 by amplitude and frequency components of the artifact within the amplified sets of bipolar limb lead and augmented lead signals LII150, LIII150, LIIII150, LAVR150, LAVL150, LAVF150 and LVX150. A pace detect output signal is applied to block 114 for A/D conversion and interrupt signals are also generated for pace pulse timers.

In FIG. 2B, the "ECG anti-alias and isolation" block 112 provides amplification of the applied signals to an extent that they may be processed in the "A/D converter circuit" block 114. Anti-aliasing filters in block 112 prevent high frequency signal components from aliasing into the ECG bandwidth. Optical isolation is also provided to protect the patient from the effects of alternating current as the signals are amplified and filtered. The optically isolated output signals are applied to the A/D converter circuit block 114, and the non-isolated output signals are applied to the "analog out" block 116.

The particular circuitry and functions of the blocks 108–118 are not of importance to the present invention and are described to show the context in which the present invention is realized in one preferred embodiment.

FIG. 1A of the '316 patent is compared to FIG. 2A of the present invention in the following description. In FIG. 1A of the '316 patent, signals developed in block 102 and related to the aVR, aVL and aVX leads of TABLE I are output from block 102 (as described below with respect to FIG. 3B) and directed to block 106. In the preferred embodiment of the present invention, as shown in FIGS. 2A and 5, these signals LAVRN and LAVRP, LAVLN and LAVLP, and LAVFN and LAVFP are not developed in block 102 and provided to block 106. Only the signals LVXN and LVXP are developed in block 102 and applied to block 106 for amplification by the circuit 400 as depicted in FIG. 4. Other differences are described as below.

Figure 3A:
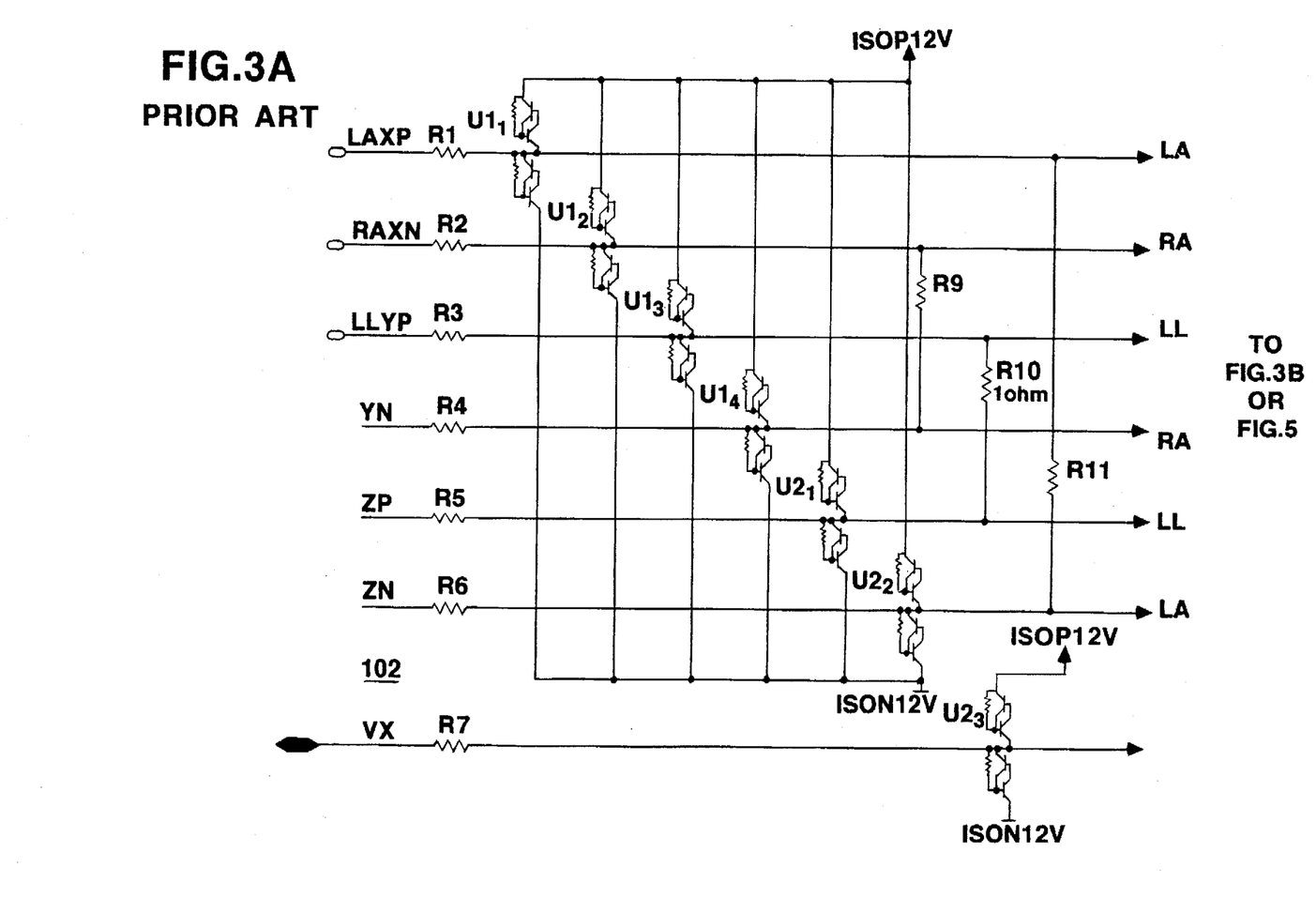
FIGS. 3A and 3B together constitute a schematic diagram illustrating the prior art lead weighting resistor network and DEFIB/ESD protection circuit block employed in a prior art implementation of the system of FIGS. 2A and 2B.
Figure 3B:
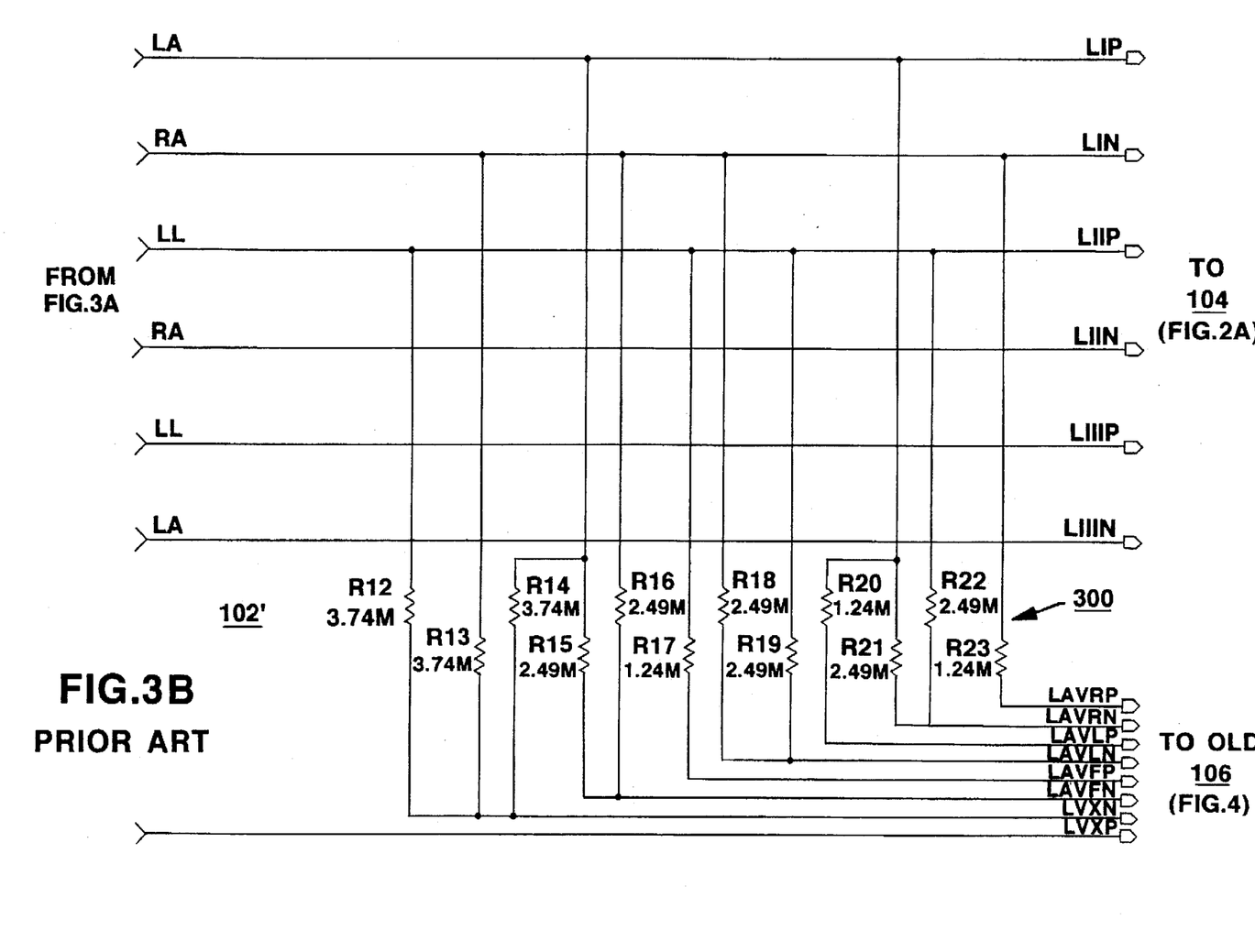

FIG. 3A depicts the first portion of block 102 common with the Model 9790 programmer and the present invention, the incoming LAXP, RAXN, LLYP, YN, ZP, ZN and VX from the skin surface limb and torso electrodes are conducted through resistors R1–R7 which preferably are 150 ohms. The input signals then pass through a high voltage, defibrillator shock protection array of SCR circuits U1$_1$, U1$_2$, U1$_3$, U1$_4$, U2$_1$, U2$_2$, and U2$_3$ as described in the above-incorporated '316 patent (FIG. 5). When a high voltage shock or signal is transmitted through the limb electrodes and onto these terminals, the SCR circuits are rendered conductive by the high voltage pulse to tie the terminals between isolated 12 volt positive and negative power supplies in power block 122. The SCR circuits therefore do not conduct unless a high voltage is on the respective electrodes, and the input signals are applied to the low impedance resistor network of resistors R9, R10 and R11 and to the circuit of FIG. 3B in the Model 9790 programmer system or to the circuit of FIG. 5 of the present invention.

One ohm resistors R9, R10 and R11 are present to configure the system 100 as a conventional lead system for deriving the leads listed in TABLE I and the optional V$_x$ lead and not as a Simson lead system for SAECG. The resistors R9–R11 can be removed to configure the system 100 as a Simson lead system employing the X+/X−, Y+/Y−, and Z+/Z− electrode and signal pairs denoted in FIG. 2A. The following description assumes the depicted conventional lead system configuration and the employment of the FIG. 3A in conjunction with FIG. 5 as constituting the circuit of block 102 in accordance with the present invention.

Continuing with the description of the prior circuit of the Model 9790 programmer, FIG. 3B shows the remaining portion of the prior lead weighting resistor network and DEFIB/ESB protection block of the '316 patent, denoted 102' for purposes of this description. The positive and negative signal pairs used to derive the lead I, lead II and lead III signals listed in TABLE I, i.e. the depicted LIP, LIN, LIIP, LIIN, LIIIP, and LIIIN signals, pass through the circuit 102' and are applied to the input terminals of block 104 as shown in FIG. 1A and 2 of the '316 patent. The LIP, LIN, LIIP, LIIN, LIIIP, and LIIIN signals are also coupled to a high impedance resistor dividing network 300 employed to combine the signals to obtain the aVR, aVL and aVF augmented lead positive and negative signal pairs LAVRP, LAVRN, LAVLP, LAVLN, LAVFP, LAVFN and LVXN used to derive the aVR, aVL and aVF augmented lead signals in the "leads AVR, AVL, AVF and VX amplifiers" block shown in FIG. 1A of the '316 patent. The weighting values of the resistors R12–R23 in circuit 102' mathematically combine the LIP, LIN, LIIP, LIIN, LIIIP, and LIIIN signals in accordance with equations (4)–(6) in TABLE I to provide the positive and negative augmented lead signals LAVRP, LAVRN, LAVLP, LAVLN, LAVFP, LAVFN, and LVXN applied to the "leads AVR, AVL, AVF and VX amplifiers" block. The LVXP signal at terminal LVXP simply passes through the circuit 102' as shown in FIG. 3 of the above-incorporated '316 patent and in FIG. 3A.

Resistors R15–R23 are high impedance, precision tolerance resistors of the values shown in FIG. 3B. Such resistors are expensive in relation to other circuit components, and signals transmitted through them are "noisy". The electrical noise arises from resistor "Johnson noise" which is related to the temperature and bandwidth and which reduces the signal-to-noise ratio in the signals passing through them.

In the prior art Model 9790 programmer implementation of system 100, the positive and negative augmented lead signal pairs, LAVRP-LAVRN, LAVLP-LAVLN, and LAVFP-LAVFN, and the LVXN-LVXP signal pair, are processed through four parallel, electrically separated, signal amplifier stages in block 106. The amplifier stage 400 for processing the LVXN and LVXP signal pair to provide the LVX150 output signal and the RECVX output signal is shown in FIG. 4 as exemplary of all four amplifier stages. An OP Amp U19 is configured as a differential amplifier 402 through resistors R63 and R64, which set the gain of differential amplifier 402, in order to subtract the signal values from one another with negligible amplification of the resulting LVX difference signal.

The resulting LVX signal is filtered in a high pass filter 404 comprising capacitor C33 and resistor R93 and applied to the positive input terminal of OP Amp U51 which is configured as a gain amplifier 406. The values of resistors R85 and R89 and capacitor C37 are selected to provide 7.5× amplification of the LVX signal. The filtered signal RECVX is also applied to an input terminal of the control and isolation block 108.

It will be understood that in the prior art system embodied in the Model 9790 programmer, three additional circuits identical to circuit 400 are contained in the block 106 which receive the signal pairs comprising LAVRN-LAVRP, LAVLN-LAVLP, and LAVFN-LAVFP signals. These amplifiers are not interconnected in any way and operate independently in parallel with one another. Attention is again directed to FIG. 1A of the '316 patent where it is shown that these signals are output from block 102 (as described above with respect to FIG. 3B) and directed to block 106. In the preferred embodiment of the present invention, as shown in FIGS. 2A and 5, these signal pairs LAVRN-LAVRP, LAVLN-LAVLP, and LAVFN-LAVFP are not developed in block 102 and provided to block 106.

The second portion of circuit 102' of block 102 of the present invention is shown in FIG. 5, and in accordance with the present invention is substituted for circuit 102' of FIG. 3B. The high impedance resistor network 300 of the prior art embodiment of block 102' shown in FIG. 3B is eliminated as far as the processing of the augmented leads is concerned. This eliminates the noise source presented by the high impedance resistors resulting in an improvement in the signal-to-noise ratio of approximately 300%.

Figure 4:
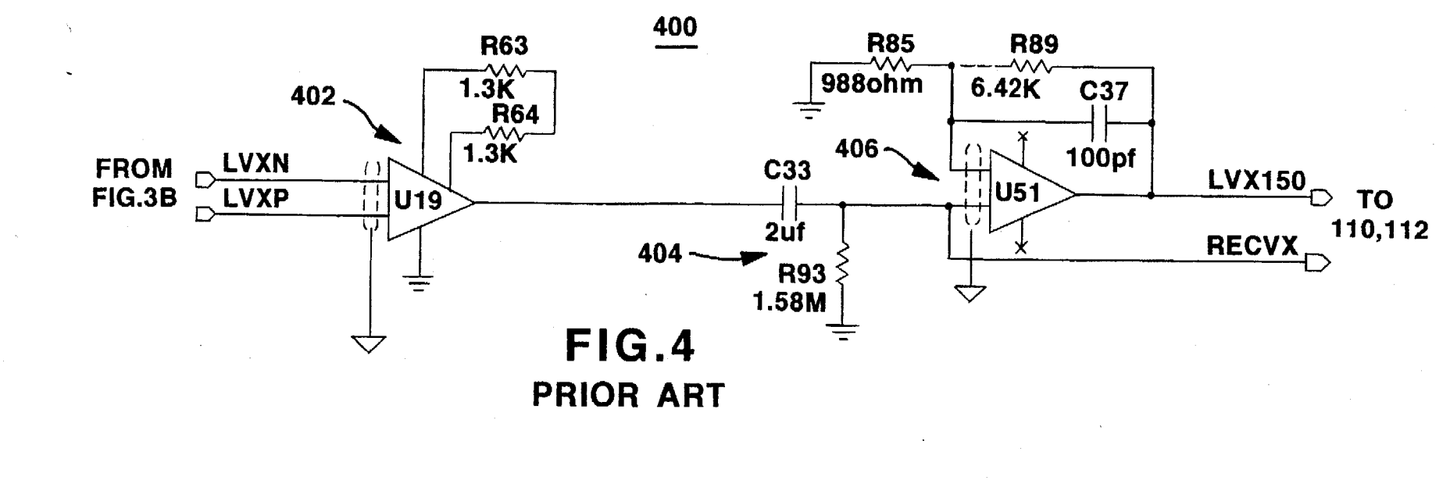
FIG. 4 is a schematic diagram of a VX amplifier circuit employed in both the prior art implementation and in the present invention implementation of the system of FIGS. 2A and 2B.
Figure 5:
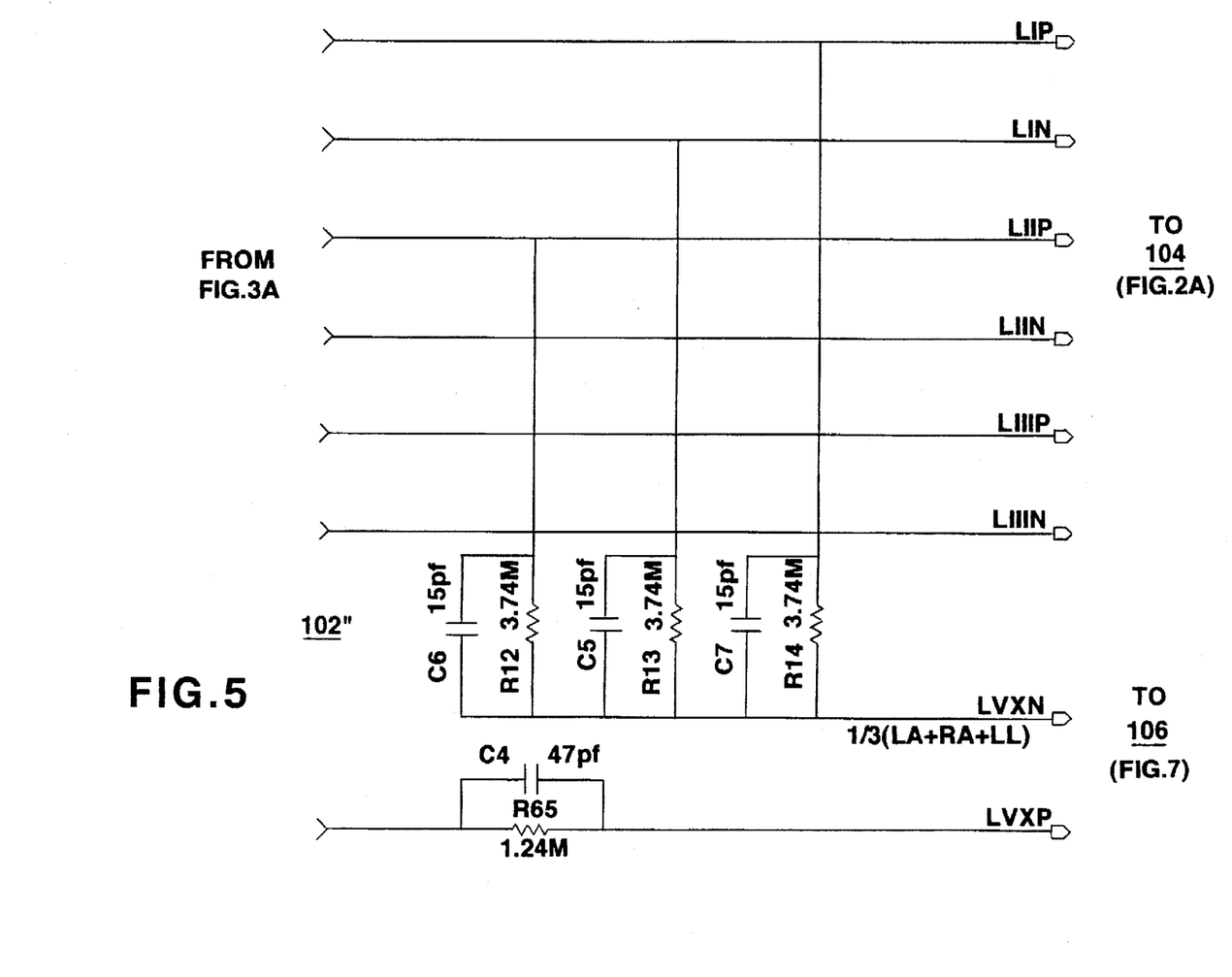
FIG. 5 is a schematic diagram illustrating a circuit network of the present invention for incorporation with the DEFIB/ESD protection circuit of FIG. 3A in substitution for the lead weighting resistor network of FIG. 3B in the system of FIGS. 2A and 2B.
Figure 6:
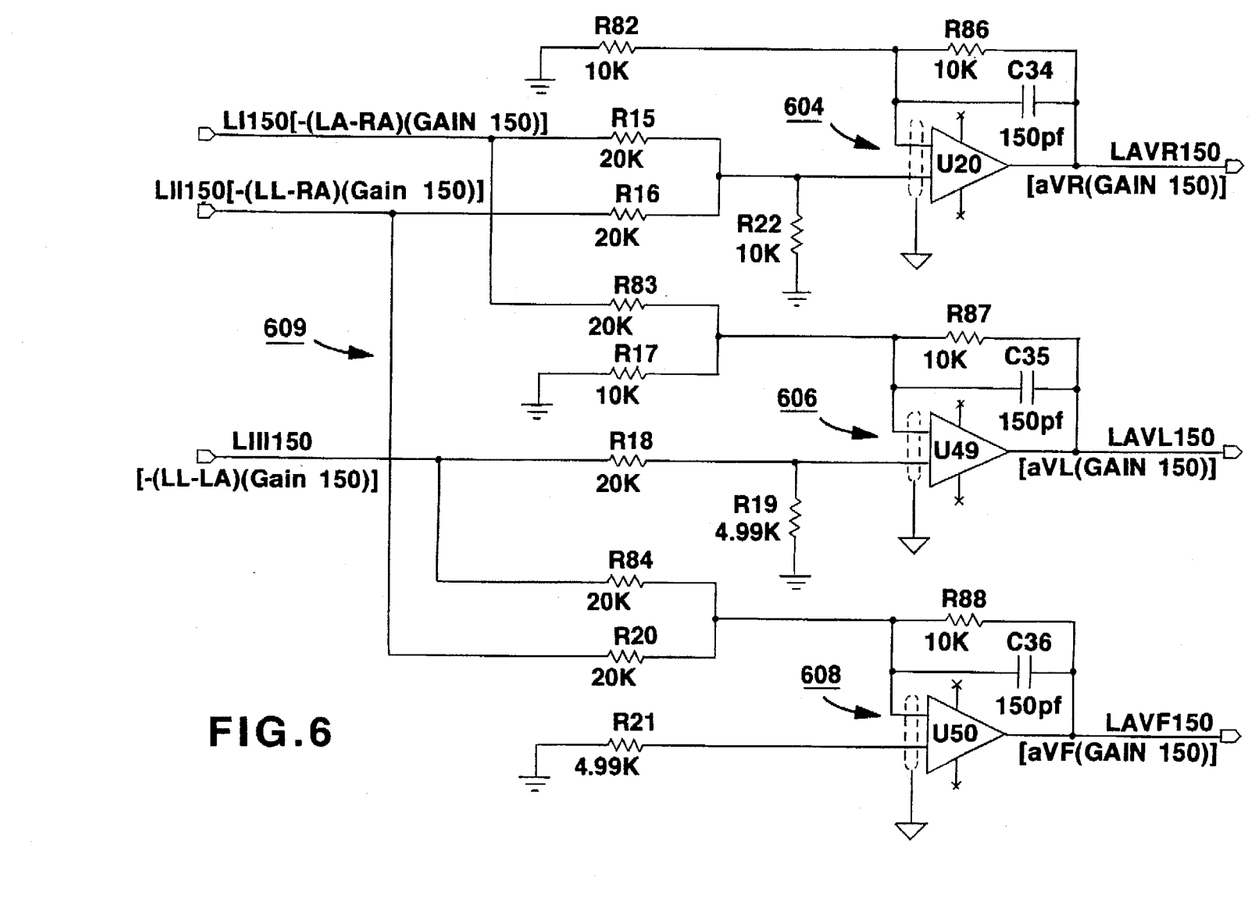
FIG. 6 is a schematic diagram of the leads aVR, aVL, and aVF resistor network and amplifiers circuits that are included with the VX amplifier circuit of FIG. 4 in accordance with the present invention for incorporation into the system of FIGS. 2A and 2B.

FIG. 6 depicts the improved leads AVR, AVL and AVF amplifier circuit of the present invention which is included in conjunction with the independently operating VX amplifier circuit of FIG. 4 as the block 106 of FIG. 2A for deriving the augmented lead signals and the VX signal. A low impedance resistor network 600 is substituted for the high impedance resistor network 300 and for three differential amplifiers, each corresponding to differential amplifier 402 of FIG. 4, for deriving the augmented lead signals, LAVR150, LAVL150 and LAVF150, from the LI150, LII150 and LIII150 signals.

The signal LVX150 is derived in block 106 in the same manner as described above using the circuit 400 of FIG. 4. In regard to the processing of the LVXN signal, the only change appears in FIG. 5, where shunt capacitors C4–C7 are provided in parallel to high impedance resistors R65 and R12–R14 in order to shunt the impedance of the resistors at high frequency. Because the impedance of a capacitor is inversely proportional to frequency, capacitance values of about 15 picofarads shunted with the resistance of 3.74 megohms creates a pole at about 23 kHz which effectively limits the gain of the amplifiers for noise frequencies, primarily created in switching power supplies, that exceed it. The processing of the LVXN and LVXP signals are otherwise unchanged, resulting in the retention of the resistors R12, R13 and R14 of the high impedance resistor network 300 as shown in FIG. 5.

At the output terminals of the circuit 102' of FIG. 5 (and at the input and output connections shown in the circuit of FIG. 3A), both the positive and negative lead I, lead II and lead III signal pairs and the RA, LA and LL limb electrodes from which these signals are obtained are denoted. Because the conventional formulas of TABLE I use the limb electrode designations as signal values, they are included in FIGS. 5 and 6 in order to show how the augmented lead signals are derived at the outputs of the operational amplifiers of the circuit of FIG. 6 used in the block 106. Note in FIG. 5 that the signal LVXN represents the combination of ⅓ (LA+RA+LL) through the common interconnection of LA, RA and LL electrodes through the resistor and capacitor network.

FIG. 2A shows the lead I signal pair, LIP (RA ELECTRODE), LIN (LA ELECTRODE), the lead II signal pair, LIIP (LL ELECTRODE), LIIN (RA ELECTRODE), and the lead III signal pair, LIIIP (LL ELECTRODE), LIIIN (LA ELECTRODE), are applied to the "leads I, II and III and X, Y, Z amps" block 104, conforming to FIG. 2A (circuit 200) of the '316 patent (with electrode designations corrected as noted above). The output signals generated by the differential operational amplifiers of block 104 are applied to block 106 are designated as follows:

TABLE II

| ELECTRODES | LEADS | DESIGNATION | |
|---|---|---|---|
| –(LA – RA) | –Lead I | LI150 | (7) |
| –(LL – RA) | –Lead II | LII150 | (8) |
| –(LL – LA) | –Lead III | LIII150 | (9) |

The negative sign, lead I, lead II and lead III signals are amplified by a factor of 150, resulting in the designation of the lead signals applied to the inputs of the circuit of block 106 as LI150, LII150 and LIII150.

In FIG. 6, three operational amplifiers 604, 606 and 608 are interconnected by low impedance resistor network 600. The amplifiers are formed of OP Amps U20, U49 and U50 each having a parallel resistor and capacitor network coupled between the negative input and the output of the OP Amp and provide 0.5× signal amplification of the signals applied at the positive and negative input terminals. The negative input terminals of Op amps U20, U49 and U50 are coupled to their respective output terminals through resistor and capacitor pairs, namely R86 and C34, R87 and C35 and R88 and C36. The positive terminals of Op amps U20, U49 and U50 are coupled to system ground through resistors R22, R19 and R21, respectively.

With respect to the derivation of LAVR150 (aVR (Gain150)), the signals -Lead I (Gain 150) and -Lead II (Gain 150) are summed through the resistors R15 and R16 and applied across resistor R22 to the positive input of the Op amp U20. The negative input of Op amp U20 is coupled to the output terminal through resistor R86 and capacitor C34 and to ground through resistor R82. With respect to the derivation of LAVL150 (aVL(Gain 150)), the signal -Lead II (Gain 150) is coupled through resistor R83, summed with the ground potential at the junction with resistor R17 and applied to the negative input of Op amp U49. The signal -Lead III (Gain 150) is applied through resistor R18 and across resistor R19 to the positive input terminal of Op amp U49. With respect to the derivation of LAVF150 (aVF(Gain 150)), the positive input terminal of Op amp U50 is coupled to ground through resistor R21, and the signals-Lead II (Gain 150) and-Lead III (Gain 150) are summed through the resistors R84 and R20 and applied to the negative input terminal of the Op amp U50.

Resistors R86–R88 are of the same resistance value, and capacitors C34–C36 are the same value. Resistors R82, R17 and R22 are twice the value of resistors R19 and R21, and the remaining resistors R15, R16, R18, R20, R83 and R84 are four times the value of resistors R19 and R21. These resistance relationships are mathematically derived in relation to the resistance of resistors R86–R88 in order to provide a gain of 0.5 in each Op am U20, U49 and U50 and result in the augmented lead signals listed in TABLE III as follows:

TABLE III aVR(Gain 150) = [RA – 0.5 (LA + LL)] or –0.5 (Lead I + Lead II) (10)
aVL(Gain 150) = [LA – 0.5 (RA + LL)] or 0.5 (Lead I – Lead III) (11)
aVF(Gain 150) = [LL – 0.5 (LA + RA)] or 0.5 (Lead II + Lead III) (12)

The circuitry of FIGS. 5 and 6 results in a number of improvements in the augmented lead signals due to the elimination of Johnson noise. The signal-to noise ratio is increased by 300% while the cost and size of the circuitry is reduced. The lower impedance resistors are also more reliable and have lower power consumption. The testability of the circuit is also improved because of the reduced number of components. The input impedance at the RA, LA, and LL limb electrodes presented to the input terminals of the Op amps of block 104 is also increased by the removal of the high impedance resistor network 300, resulting in better signal processing performance for the limb lead and augmented lead signals, particularly when the patient's skin-electrode impedance varies from limb electrode to limb electrode while preserving the ability to detect the pacing pulse. Although the present invention is implemented in a conventional limb lead and augmented lead ECG system, it will be understood that it may be practiced in an unconventional use or designation of leg and arm electrodes and electrode pairs.

While the invention has been described above in connection with a particular embodiment, one skilled in the art will appreciate that the invention is not necessarily so limited. It will thus be understood that numerous other embodiments, examples, uses, modifications of, and departures from the teachings disclosed may be made, without departing from the spirit and scope of the present invention as claimed herein.

We claim:

1. An apparatus for deriving augmented lead electrocardiograph (ECG) signals from electrical signals sensed at three skin surface, limb electrodes attached to a patient's limbs without the use of a high impedance resistor network, comprising:

means for combining first, second and third pairs of the three limb electrodes to provide first, second and third, positive and negative, limb lead signal pairs;

means for combining and amplifying the first positive and negative limb lead signal pair into a first limb lead signal (LI);

means for combining and amplifying the second positive and negative limb lead signal pair into a second limb lead signal (LII);

means for combining and amplifying the third positive and negative limb lead signal pair into a third limb lead signal (LIII); and low impedance resistor network and amplifier means for combining the first, second and third lead limb signals into augmented lead signals.

2. The apparatus of claim 1, wherein said low impedance resistor network and amplifier means further comprises:

a first operational amplifier configured as a differential amplifier having a gain of 0.5 and positive and negative input terminals and a first output terminal; and a first low impedance network branch of said low impedance resistor network coupled to said positive input terminal of said first operational amplifier for summing the first and second lead signals, wherein the first augmented lead signal (aVR) is derived at the first output terminal in accordance with the formula: aVR=−0.5 (LI+LII).

3. The apparatus of claim 2, wherein said low impedance resistor network and amplifier means further comprises:

a second operational amplifier configured as a differential amplifier having a gain of 0.5 and positive and negative input terminals and a second output terminal; and a second low impedance branch coupled to said positive and negative input terminals of said second operational amplifier for summing the first and second lead signals, wherein the second augmented lead signal (aVL) is derived in accordance with the formula: aVL=0.5 (LI−LIII).

4. The apparatus of claim 3, wherein said low impedance resistor network and amplifier means further comprises:

a third operational amplifier configured as a differential amplifier having a gain of 0.5 and positive and negative input terminals and a third output terminal; and a third low impedance branch of coupled to said negative input terminal of said third operational amplifier for summing the second and third lead signals, wherein the third augmented lead signal (aVF) is derived in accordance with the formula: aVF=0.5 (LII+LIII).

5. An apparatus for deriving augmented lead electrocardiograph (ECG) signals from electrical signals sensed at skin surface, right and left arm electrodes designated RA and LA and a leg electrode designated LL without the use of a high impedance resistor network comprising:

means for sensing a fast limb lead signal pair from the RA and LA limb electrodes;

means for sensing a second limb lead signal pair from the RA and LL limb electrodes;

means for sensing a third limb lead signal pair from the LA and LL limb electrodes;

means for amplifying and subtracting the first limb lead signal pair to derive a first, amplified limb lead signal (LI);

means for amplifying and subtracting the second limb lead signal pair to derive a second, amplified limb lead signal (LII);

means for amplifying and subtracting the third limb lead signal pair to derive a third, amplified limb lead signal (LIII);

first low impedance network and amplifier means for combining the first and second lead signals for deriving a first augmented lead signal (aVR) in accordance with the formula: aVR=−0.5 (LI+LII);

second low impedance network and amplifier means for combining the first and third lead signals for deriving a second augmented lead signal (aVL) in accordance with the formula: aVL=0.5 (LI−LIII); and third low impedance network and amplifier means for combining the second and third lead signals for deriving a third augmented lead signal (aVF) in accordance with the formula: aVF=0.5 (LII+LIII).

6. A method of deriving augmented lead electrocardiograph (ECG) signals from electrical signals sensed at three skin surface, limb electrodes attached to a patient's limbs without the use of a high impedance resistor network, comprising the steps of:

combining first, second and third pairs of the three limb electrodes to provide first, second and third positive and negative limb lead signal pairs;

combining and amplifying the first positive and negative limb lead signal pair into a first limb lead signal (LI);

combining and amplifying the second positive and negative limb lead signal pair into a second limb lead signal (LII);

combining and amplifying the third positive and negative limb lead signal pair into a third limb lead signal (LIII); and combining the first, second and third lead limb signals LI, LII and LIII into augmented lead signals through a low impedance resistor network and operational amplifier.

7. A method of deriving augmented lead electrocardiograph (ECG) signals from electrical signals sensed at skin surface, right and left arm electrodes designated RA and LA and a leg electrode designated LL without the use of a high impedance resistor network, comprising the steps of:

sensing a first limb lead signal pair from the RA and LA limb electrodes;

sensing a second limb lead signal pair from the RA and LL limb electrodes;

sensing a third limb lead signal pair from the LA and LL limb electrodes;

amplifying and subtracting the first limb lead signal pair to derive a first, amplified limb lead signal (LI);

amplifying and subtracting the second limb lead signal pair to derive a second, amplified limb lead signal (LII);

amplifying and subtracting the third limb lead signal pair to derive a third, amplified limb lead signal (LIII);

deriving a first augmented lead signal (aVR) by combining the first and second limb lead signals in a first low impedance network and amplifier in accordance with the formula: $aVR = -0.5\,(LI + LII)$;

deriving a second augmented lead signal (aVL) by combining the first and third limb lead signals in a second low impedance network and amplifier in accordance with the formula: $aVL = 0.5\,(LI - LIII)$; and deriving a third augmented lead signal (aVF) by combining the second and third limb lead signals in a third low impedance network and amplifier in accordance with the formula: $aVF = 0.5\,(LII + LIII)$.

* * * * *

UNITED STATES PATENT AND TRADEMARK OFFICE
CERTIFICATE OF CORRECTION

PATENT NO. : 5,709,213
DATED : Jan. 20, 1998
INVENTOR(S) : John M. Kruse et al.

It is certified that error appears in the above-identified patent and that said Letters Patent is hereby corrected as shown below:

C. 11 L. 29      "provide fast, second and third," to be changed to "provide first, second and third,"
C. 12 L. 15      "sensing a fast limb" to be changed to "sensing a first limb"

Signed and Sealed this

Sixteenth Day of November, 1999

Attest:

Q. TODD DICKINSON

*Attesting Officer*      *Acting Commissioner of Patents and Trademarks*